United States Patent
Kivatinos et al.

(10) Patent No.: US 11,410,761 B2
(45) Date of Patent: Aug. 9, 2022

(54) AUTOMATED DETECTION OF MEDICATION INTERACTIONS

(71) Applicant: drchrono Inc., Sunnyvale, CA (US)

(72) Inventors: Daniel Kivatinos, Mountain View, CA (US); Michael Nusimow, Mountain View, CA (US); Martin Borgt, Sunnyvale, CA (US); Soham Waychal, Sunnyvale, CA (US)

(73) Assignee: DRCHRONO INC., Sunnyvale, CA (US)

( * ) Notice: Subject to any disclaimer, the term of this patent is extended or adjusted under 35 U.S.C. 154(b) by 29 days.

(21) Appl. No.: 16/457,787

(22) Filed: Jun. 28, 2019

(65) Prior Publication Data

US 2020/0035343 A1 Jan. 30, 2020

Related U.S. Application Data

(60) Provisional application No. 62/703,880, filed on Jul. 27, 2018.

(51) Int. Cl.
| | |
|---|---|
| *G16H 20/10* | (2018.01) |
| *G16H 10/60* | (2018.01) |
| *G16H 15/00* | (2018.01) |

(52) U.S. Cl.
CPC ............ *G16H 20/10* (2018.01); *G16H 10/60* (2018.01); *G16H 15/00* (2018.01)

(58) Field of Classification Search
CPC ......... G16H 20/10; G16H 10/60; G16H 15/00
USPC ........................................................ 705/2–3
See application file for complete search history.

(56) References Cited

U.S. PATENT DOCUMENTS

| | | | | |
|---|---|---|---|---|
| 2001/0001144 A1* | 5/2001 | Kapp | ..................... | G16H 20/17 705/3 |
| 2002/0040282 A1* | 4/2002 | Bailey | ..................... | G16H 40/63 702/188 |
| 2006/0261145 A1* | 11/2006 | Robertson | .............. | G16H 10/60 235/375 |
| 2010/0274586 A1* | 10/2010 | Choi | ..................... | G06Q 10/10 705/3 |
| 2018/0322251 A1* | 11/2018 | Allen | ..................... | G16H 70/40 |

\* cited by examiner

*Primary Examiner* — Michael Tomaszewski
(74) *Attorney, Agent, or Firm* — James J. DeCarlo; Greenberg Traurig, LLP

(57) ABSTRACT

A computer system may parse a set of medical events of a patient and determine when the patient has been taking a first medication and a second medication. The computer system may determine the duration of time in which the patient has been taking the first medication. An expected duration of time for the course of treatment may be provided. When it is determined that the actual course of treatment differed from the expected duration of treatment, then the system may flag a potential drug interaction. When enough of these flags are determined, an indication of a potential drug interaction may be stored and a prompt or notification sent to other health practitioners about the potential drug interaction.

20 Claims, 3 Drawing Sheets

AUTOMATED DETECTION OF MEDICATION INTERACTIONS

CROSS-REFERENCE TO RELATED APPLICATIONS

This application claims the benefit of U.S. Provisional Patent Application No. 62/703,880, filed Jul. 27, 2018, which is hereby incorporated by reference in its entirety.

FIELD OF THE INVENTION

The present invention relates to a computer system and method for using software-based protocols to detect medication interactions.

BACKGROUND

Drug interactions, the interaction of a first drug with a second drug, present a serious concern to human health. The traditional method of identifying drug interactions is through clinical study. However, this is time consuming and expensive. It would be desirable to provide a system of tracking and analyzing medical events to automatically determine likely occurrences of drug interactions.

SUMMARY OF THE INVENTION

Some embodiments relate to using a computer system to automatically detect new drug interactions between a first medication and second medication through the application and analysis of big data. In some embodiments, one signal that is analyzed is whether a second drug was being taken and whether medical events of a patient indicate that the duration that the patient took a course of treatment with a medication was outside the range of expected durations. This may indicate a negative interaction that influenced the patient to end the course of treatment early.

In some embodiments, electronic records of a plurality of medical events of a patient are received. The medical events are parsed to identify a first medical event for the patient filling a prescription for a first medication. It is then determined that this first medical event is the start of a course of treatment of the patient. The end of that course of treatment is then determined, and the duration of the course of treatment is compared to an expected duration of the course of treatment. If the actual duration of the course of treatment is outside of the expected duration of the course of treatment, then a value may be stored indicating a potential drug interaction. When a sufficient number of these flags are stored as compared with incidences where there was no flag, then a prompt may be sent to other health practitioners that a potential drug interaction may exist.

In some embodiments, a health practitioner who is treating the patient is prompted to provide input about whether a drug interaction may exist. In this embodiment, when enough health practitioners have inputted an answer that there is a potential drug interaction between a first and second medication, then a prompt may be sent to other health practitioners that a potential drug interaction may exist.

DETAILED DESCRIPTION

Figure 1:
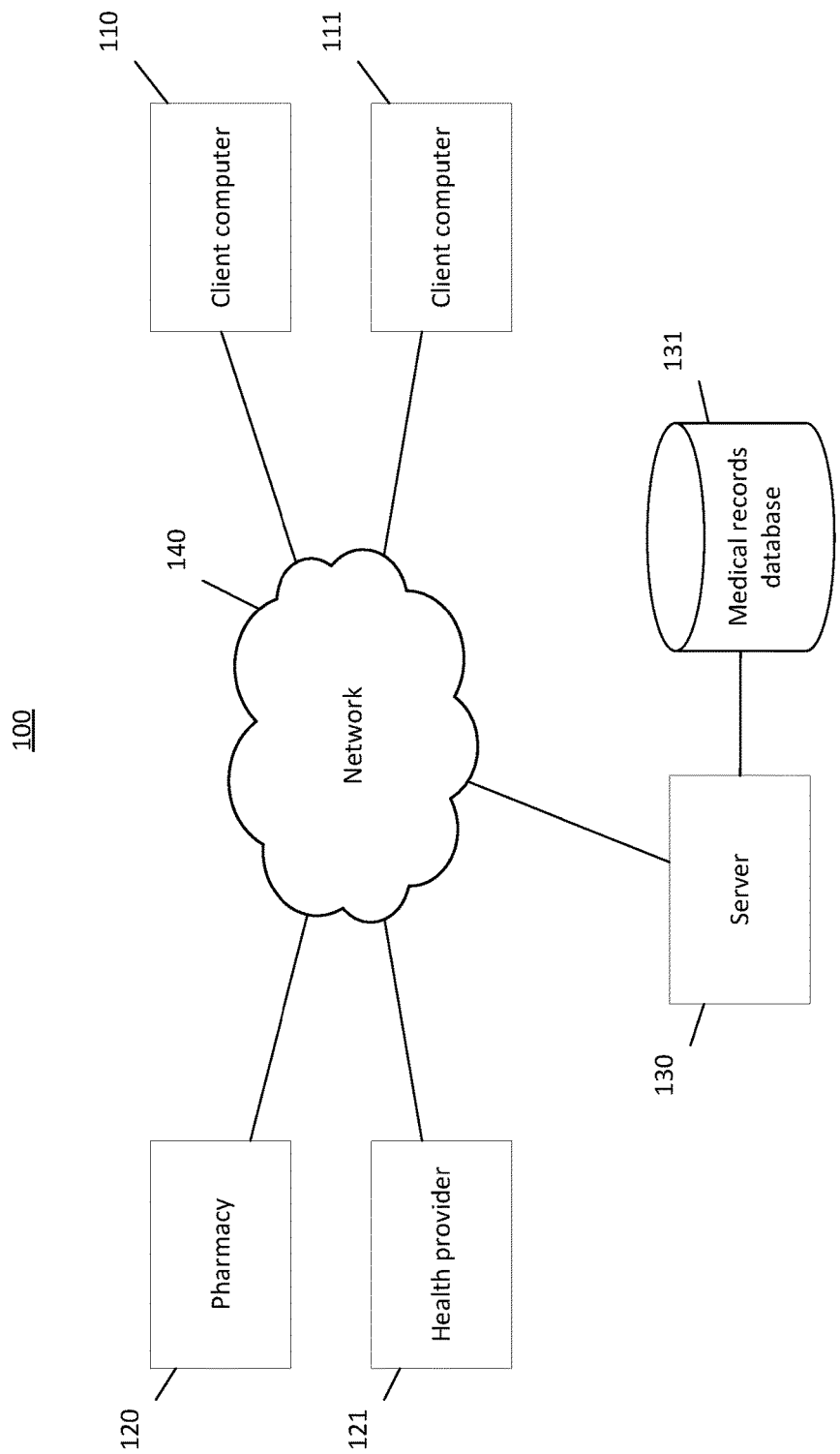
FIG. 1 illustrates an exemplary network environment where some embodiments of the invention may operate.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

FIG. 1 illustrates an exemplary environment 100 in which embodiments of the invention may operate. Environment 100 includes two client computers 110, 111 that display information to users. Users may be health practitioners, such as doctors, nurses, dieticians, and other health practitioners, patients, or administrators. Client computers 110, 111 are connected over a network 140 with pharmacy 120, health provider 121, and server 130. The network 140 may be, for example, a local network, intranet, wide-area network, the Internet, wireless network, wired network, Wi-Fi, Bluetooth, or other networks. Server 130 may be connected to an electronic medical records database 131 that stores medical records of one or more patients. Server 130 may receive notifications of medical events from pharmacy 120, such as notifications of the patient filling a prescription. Notifications may include a transaction notification that the patient purchase a prescription or non-prescription medication. Server 130 may receive notifications of medical events from health provider 121, such as notifications of the patient attending an appointment with a health practitioner or having a medical procedure performed. Server may record the medical events in an electronic record stored in medical records database 131. The electronic record of a patient may include a chronological listing of the medical events incurred by the patient.

Client computers 110, 111 may transmit to and receive data from server 130. Client computers 110, 111 may display electronic records downloaded or streamed from server 130 to users. Client computers 110, 111 may be, for example, mobile devices, desktop computers, laptops, smart devices, tablets, and other computer systems. Although two client computers 110, 111 and one server 130 are illustrated, many more client computers and servers may be in environment 100.

Figure 2A:
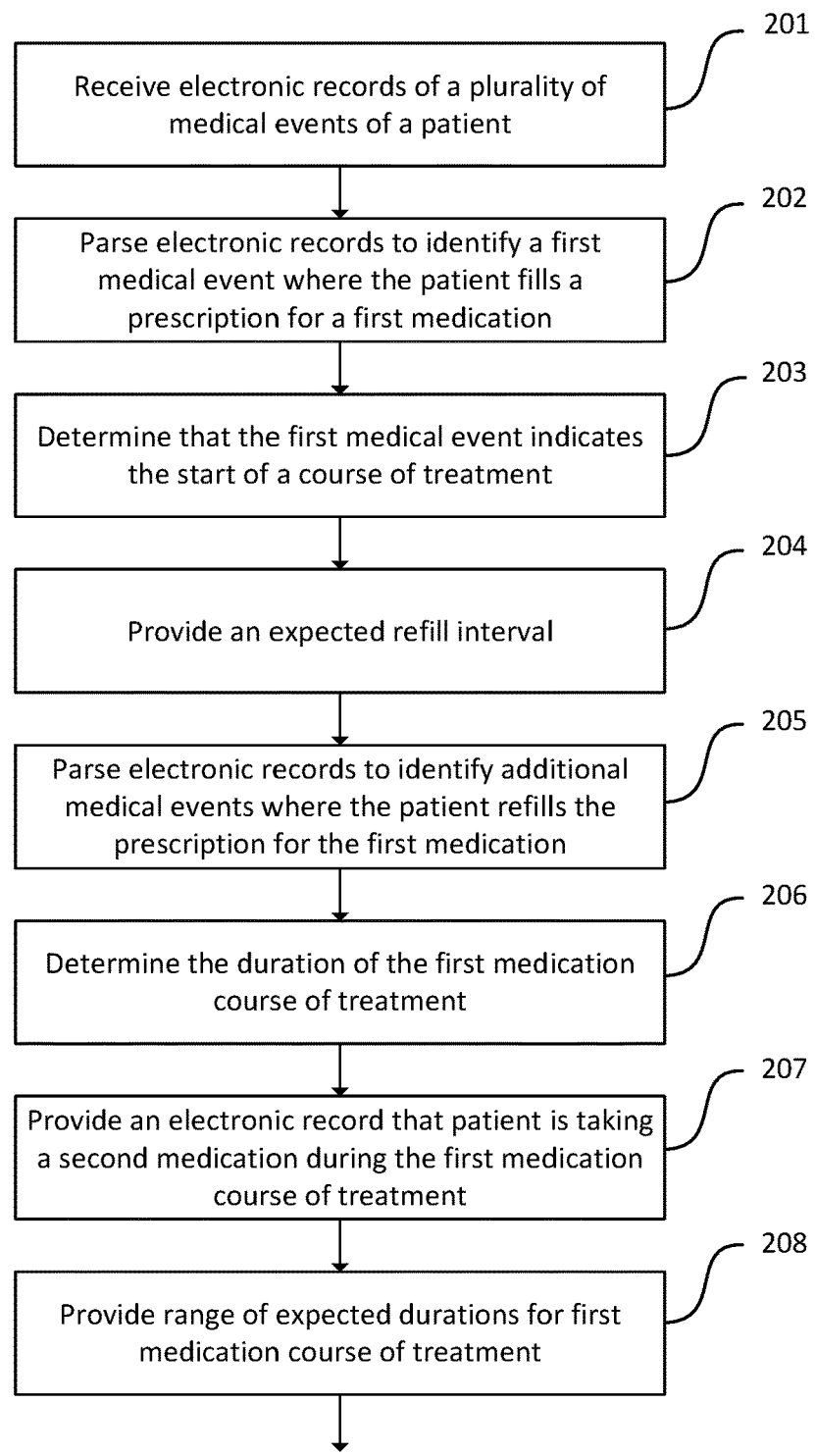
FIGS. 2A-B illustrate an exemplary method that may be performed to analyze a set of medical events to determine interactions between medications.
Figure 2B:
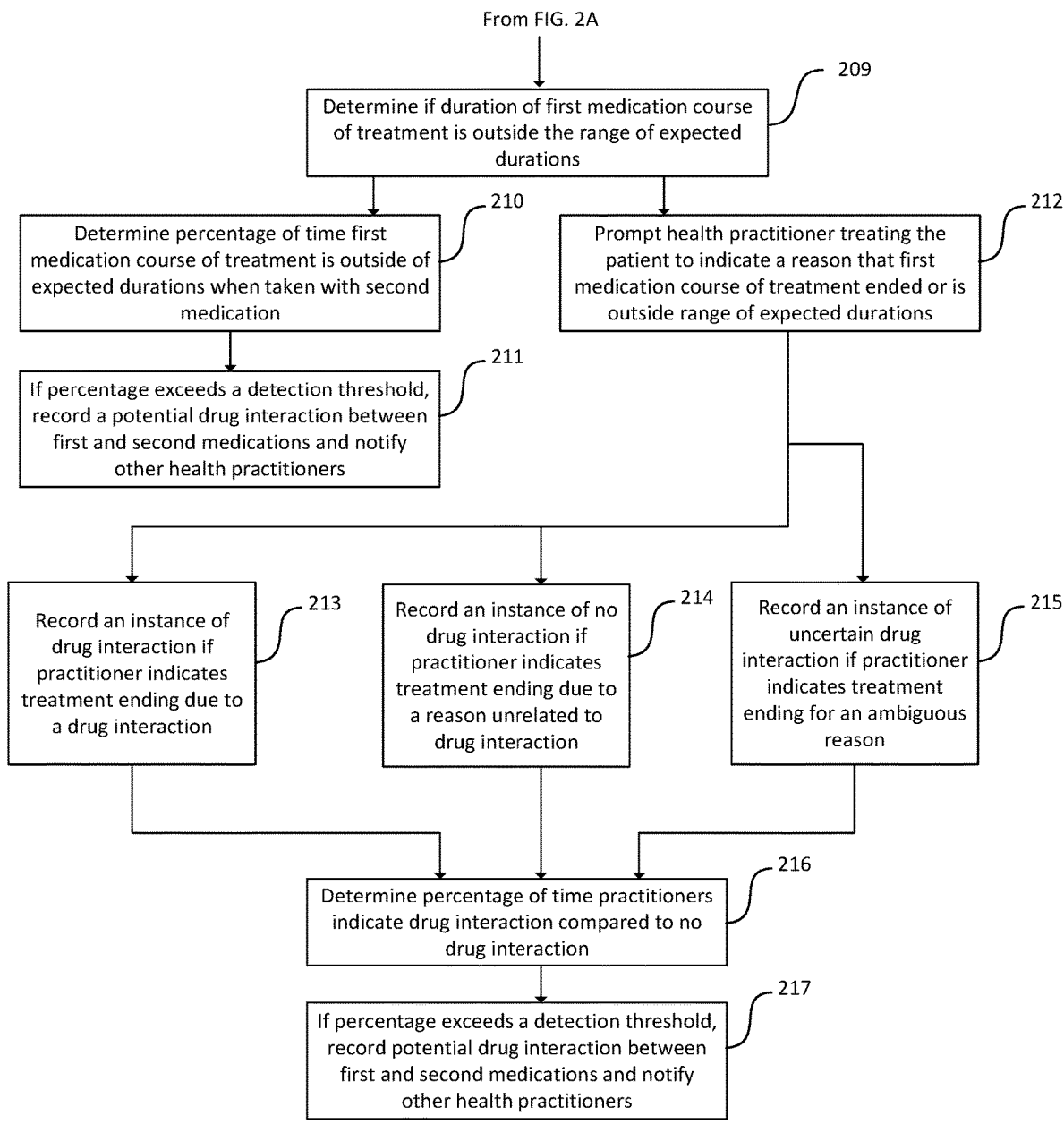

FIGS. 2A-B illustrates an exemplary method 200 of detecting drug interactions by computer analysis of a series of medical events.

In step 201, electronic records of a plurality of medical events of a patient may be received. The medical events may include a date, time, and description of the event. Medical events may include filling a prescription, attending an appointment with a health provider, having a medical procedure performed, obtaining a lab test, and other medical events. In some embodiments, one or more, or all, of the medical events are billing claims made to a payer, such as a health insurance company, Medicaid, or Medicare. Billing claims are claims made for payment for a medical product or service. Billing claims may include standardized billing codes, where a standardized alphanumeric sequence represents a specific product or service.

In some embodiments, the electronic records may be displayed to a user, such as a patient or practitioner, on a mobile device.

In step 202, the electronic records of the plurality of medical records are parsed to identify a first medical event for the patient, where the first medical event represents the patient filling a prescription for a first medication. This medical event may have been transmitted from a pharmacy when the patient ordered or pricked up the prescription medication. In some embodiments, the first medical event may include a billing code.

In some embodiments, parsing may be performed by a parser, which is a software computer program that parses text. A parser may include a lexical analyzer for splitting text into tokens. In some embodiments, parsing may be performed by using regular expressions. In some embodiments, parsing may be performed by using machine learning, natural language processing, or statistical methods for analyzing text.

In step 203, it is determined that the first medical event indicates that the patient has started a course of treatment using the first medication. In some embodiments, this is determined by checking that the first medical event is the first filling of the prescription for the medication within a threshold period of time. For instance, the system may check that there have been no prior medical events in the electronic records for the patient filling a prescription for the first medication within a threshold period of time prior to the first medical event.

In step 204, an expected refill interval for the prescription is provided. In some embodiments, the expected refill interval may be 7 days, 10 days, 15 days, 20 days, 30 days, 60 days, 90 days, or other intervals. Moreover, the expected refill interval may have a margin of error for if the patient forgets to take the medication for a few days and therefore takes longer than expected to need a refill. For example, a medication that comes with enough dosages for 30 days might have an expected refill interval of 35 days given that some patients may take longer than 30 days to seek a refill.

In step 205, the electronic records of the plurality of medical events are parsed to identify additional medical events for the patient filling a prescription for the first medication, where the additional medical events occur after the first medical event. Moreover, computer system may check that the additional medical events occur within the expected refill interval of at least one other of the additional medical events or the first medical event. This helps determine that the additional medical events are part of the same course of treatment with the first medication as the first medical event because the various medical events form a chain with no medical event outside a refill interval of another medical event for obtaining the prescription.

In some embodiments, alternative methods may be used to determine the length of treatment of the patient with the first medication. For example, statistical methods may be performed to detect whether each event where the prescription is filled occurs within an expected time period, without occurring too many standard deviations away from the mean time to fill.

In step 206, the duration of the first medication course of treatment of the patient is determined. In some embodiments, this is determined by examining the time interval between the first medical event and the chronologically last of the additional medical events, where the additional medical events are connected in a chain of medical events within a refill interval of another refill event.

In step 207, an electronic record that the patient is taking a second medication during the first medication course of treatment is provided. The electronic record may be an entire health record or may be a short text, data, or graphical notification. This electronic record may be provided from, for example, pharmacy 120, health provider 121, server 130, or clients 110, 111.

In some embodiments, the first medication and second medication are for treating the same condition. In some embodiments, the first medication and second medication are for treating different conditions.

In step 208, a range of expected durations of the first medication course of treatment are provided. In some embodiments, the range of expected durations is provided in terms of the number of refills, such as 0, 1, 2, 3, 4, or more refills. Ranges may be provided such as 0-1, 1-2, 2-3, 0-2, 1-3, 2-4, 1-3, or 2-5 refills. In some embodiments, the range of expected durations is provided in terms of time, such as 7 days, 10 days, 15 days, 20 days, 30 days, 45 days, 50 days, 60 days, 90 days, or other intervals. In some embodiments, a specific number is provided for the expected duration of the first medication course of treatment such as exactly 0 refills, exactly 30 days, or so forth.

In step 209, it is determined if the duration of the first medication course of treatment is outside of the range of expected durations of the first medication course of treatment. For example, if the expected duration of the first medication course of treatment is 2 refills, but the patient obtains 0 refills, then the actual duration of the first medication course of treatment is outside the expected range. The computer system may compare the duration of the first medication course of treatment with the range of expected durations of the first medication course of treatment to make this determination. A detection of the actual course of treatment ending earlier than an expected duration of treatment indicates that the patient stopped taking the medication early and may indicate that the patient was suffering from side effects due to a drug interaction.

In some embodiments, in step 209, only a first medication course of treatment ending earlier than the expected duration is flagged. In some embodiments, in step 209, only a first medication course of treatment ending later than the expected duration is flagged.

In some embodiments, the range of expected durations of the first medication course of treatment depends on patient demographics, such as age, gender, weight, other diseases being present, whether the patient is a child, and so on.

Two different modes of operation may be provided in exemplary method 200. In a first mode of operation, the detection of the duration of the first medication course of treatment being outside the expected range is stored as a potential indicator of a drug interaction. In a second mode of operation, the patient's health provider is prompted to answer questions about why the course of treatment was discontinued before an indicator of a potential drug interaction is stored.

In the first mode of operation, in step 210, the detection of the first medication course of treatment falling outside the expected duration of treatment is treated as an indication of a potential drug interaction. While there may be other reasons that the course of treatment may end early or late, over a large dataset the other, non-drug interaction reasons for the variation average out, so that this remains a good signal of drug interactions. The computer system determines the percentage of times there was a detected drug interaction between the first medication and second medication, where the detected drug interaction is based on the duration of the first medication course of treatment being outside the expected duration, compared to there being no detected drug interaction between the first medication and second medication, indicated by the duration of the first medication course of treatment being within the expected duration. This determines a percentage of time of detected potential drug interactions.

In step 211, following step 210, when the percentage of time of detected drug interactions exceeds an interaction detection threshold, an indication of the potential drug interaction is stored and a notification is transmitted to other health practitioners who prescribe the first medication that there is a potential interaction with the second medication.

In the second mode of operation, in step 212, the computer system prompts a health practitioner who is treating the patient to indicate via user interface elements a reason that the first medication course of treatment of the patient ended, or is outside the range of expected durations. A computer device used by the health practitioner may display to the health practitioner at least three different types of answers, a first type of answer corresponding to there being a drug interaction between the first medication and second medication, a second type of answer corresponding to there being no drug interaction between the first medication and second medication, and a third type of answer corresponding to that it cannot be determined if there was a drug interaction between the first medication and second medication.

In some embodiments, one potential answer choice of the first type may be "medication turned out to be incompatible due to interactions."

In some embodiments, potential answer choices of the second type may be: "patient got better," "patient on to new trajectory of disease process as planned," "patient on to new trajectory of disease process as unplanned," "diagnosis changed," and "medication didn't work for patient."

In some embodiments, potential answer choices of the third type may be: "patient went to a different doctor," "patient died," and "other."

In step 213, when the first type of answer is received from the practitioner, a value is stored indicating a detected drug interaction between the first medication and second medication.

In step 214, when the second type of answer is received from the practitioner, a value is stored indicating no detected drug interaction between the first medication and second medication.

In step 215, when the third type of answer is received from the practitioner, a value is stored indicating that it cannot be determined if there was a drug interaction between the first medication and second medication.

In step 216, the health practitioner's selection of the first answer type is treated as an indication of a potential drug interaction. The computer system determines the percentage of times there was a detected drug interaction between the first medication and second medication, as reported by health practitioners through answer choices of the first type, compared to there being no detected drug interaction between the first medication and second medication, as reported by health practitioners through answer choices of the second type, to determine a percentage of time of detected drug interactions. Answer choices of the third type, which are ambiguous, may be ignored and the values optionally thrown out before this analysis.

In step 217, following step 216, when the percentage of time of detected drug interactions exceeds an interaction detection threshold, an indication of the potential drug interaction is stored and a notification is transmitted to other health practitioners who prescribe the first medication that there is a potential interaction with the second medication.

In some embodiments, the interaction detection threshold is configurable. Moreover, the interaction detection threshold may be derivable using mathematical methods.

In some embodiments, the interaction detection threshold is modifiable based on ground-truth determinations about whether the system correctly detected a drug interaction or not. The computer system may receive ground-truth feedback about whether a drug interaction between the first medication and second medication is an actual drug interaction. The interaction detection threshold may be adjusted based on the ground-truth feedback.

In some embodiments, user input of a desired level of statistical significance of the detection of drug interaction may be received. The computer system may automatically adjust the interaction detection threshold based on the desired level of statistical significance.

In some embodiments, drug interactions may depend on patient demographics, and the method 200 may detect a drug interaction between the first medication and second medication for patients in a first demographic group but not for patients in a second demographic group.

In some embodiments, safeguards may be provided for when another practitioner wants to prescribe a drug for which a drug interaction may apply. A request may be received from a second health practitioner to prescribe a first medication to a second patient. The computer system may detect that the second patient is currently taking a second medication for which a potential interaction with the first medication has been detected. The second health practitioner may be notified that there is a potential drug interaction between the first medication and second medication. The computer system may require the second health practitioner to confirm prescribing of the first medication before the first medication is prescribed and submitted to a pharmacy.

The terminology used herein is for the purpose of describing particular aspects only and is not intended to be limiting of the disclosure. As used herein, the singular forms "a," "an," and "the" are intended to comprise the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

While the invention has been particularly shown and described with reference to specific embodiments thereof, it should be understood that changes in the form and details of the disclosed embodiments may be made without departing from the scope of the invention. Although various advantages, aspects, and objects of the present invention have been discussed herein with reference to various embodiments, it will be understood that the scope of the invention should not be limited by reference to such advantages, aspects, and objects. Rather, the scope of the invention should be determined with reference to patent claims.

What is claimed:

1. A non-transitory computer-readable medium comprising instructions for detecting interactions between medications, the non-transitory computer-readable medium comprising instructions for:

receiving, at a server over a network, first electronic records of a plurality of medical events of a patient, from a database, each of the medical events including a date and a text description, at least one of the medical events indicating the patient filling a prescription, at least one of the medical events indicating an appointment with a health provider, the first electronic records having a first record type;

parsing, by a lexical analyzer implemented on the server, the received first electronic records into first tokens, wherein the lexical analyzer comprises a machine learning model and a natural language processing model, and wherein the tokenizing is based on results of the machine learning model and the natural language processing model, the first tokens having a first token type;

identifying a first medical event, from the tokenized first electronic records, wherein the first medical event comprises the patient filling a prescription for a first medication;

determining the presence of one or more medical events related to the first medical event in the tokenized first electronic records;

identifying, from the tokenized first electronic records, one or more related medical events associated with the first medication, wherein the one or more related medical events comprise the patient filling a prescription for the first medication;

determining that the first medical event indicates that the patient has started a course of treatment using the first medication based on the date associated with the first medical event, the presence determination and the related medical events, wherein the determining comprises:

determining a threshold period of time for the first medical event;
 identifying one or more related events that fall within the determined threshold period of time;
 receiving an expected refill interval for the prescription; and
 identifying the related medical events occurring after the first medical event, the related medical events occurring within the expected refill interval of at least one other of the related medical events or the first medical event;

determining, by the server, a duration of the first medication course of treatment of the patient based on statistically evaluating refill intervals of the related medical events, wherein the evaluating comprises:

calculating a maximum deviation value based on the time to fill for each related medical event;
 detecting if each of the related medical events occurred within the calculated maximum deviation value of the expected refill interval;
 calculating the time interval between the first medical event and the chronologically last of the related medical events, wherein the chronologically last of the related medical events is based on the detecting of related medical events within the calculated deviation value of the expected refill interval;

receiving, at the server, a notification from a pharmacy device, wherein the notification comprises a second electronic record that the patient is taking a second medication, the second electronic record being of a second record type different than the first record type;

parsing, by the lexical analyzer, the second electronic record into second tokens based on results of the machine learning model and the natural language processing model, the second tokens having a second token type that is the same as the first token type;

determining, based on the tokenized second electronic record, that the patient is taking the second medication during the first medication course of treatment;

identifying a range of expected durations of the first medication course of treatment;

determining if the duration of the first medication course of treatment is outside of the range of expected durations of the first medication course of treatment;

when it is determined that the duration of the first medication course of treatment is outside of the range of expected durations of the first medication course of treatment, storing, in the database, a value indicating a potential drug interaction;

prompting a health practitioner, on a health provider device, to indicate via user interface elements a reason that the first medication course of treatment of the patient ended, comprising displaying to the health practitioner at least three different types of answers, a first type of answer corresponding to there being a drug interaction between the first medication and second medication, a second type of answer corresponding to there being no drug interaction between the first medication and second medication, and a third type of answer corresponding to that it cannot be determined if there was a drug interaction between the first medication and second medication;

when the first type of answer is received from the health practitioner on the health provider device, storing, on the database, a value indicating a detected drug interaction between the first medication and second medication;

when the second type of answer is received from the health practitioner on the health provider device, storing, on the database, a value indicating no detected drug interaction between the first medication and second medication;

when the third type of answer is received from the health practitioner on the health provider device, storing, on the database, a value indicating that it cannot be determined if there was a drug interaction between the first medication and second medication;

retrieving, from the database, one or more potential drug interaction values;

determining, by interaction analysis, based at least partly on the retrieved potential drug interaction values, a percentage of times there was a detected drug interaction between the first medication and second medication compared to there being no detected drug interaction between the first medication and second medication to determine a percentage of time of detected drug interactions;

detecting, by interaction analysis, an interaction when the percentage of time of detected drug interactions exceeds an interaction detection threshold;

transmitting, from the server over the network, a notification to one or more health provider devices or one or more pharmacy devices, wherein the notification informs other health practitioners who prescribe the first medication that there is a potential interaction with the second medication; and adjusting, the interaction detection threshold in the interaction analysis, wherein the modifying is based on feedback indicating a correctly detected interaction.

2. The non-transitory computer-readable medium of claim 1, further comprising instructions for:

receiving ground-truth feedback for whether a detected drug interaction between the first medication and second medication is an actual drug interaction between the first medication and second medication;

adjusting the interaction detection threshold based on the ground-truth feedback.

3. The non-transitory computer-readable medium of claim 1, further comprising instructions for:

receiving user input of a desired level of statistical significance;

automatically adjusting the interaction detection threshold based on the desired level of statistical significance.

4. The non-transitory computer-readable medium of claim 1, further comprising instructions for:

detecting a drug interaction between the first medication and second medication for patients in a first demographic group but not for patients in a second demographic group.

5. The non-transitory computer-readable medium of claim 1, further comprising instructions for:

displaying the first electronic records of the plurality of medical events on a mobile device.

6. The non-transitory computer-readable medium of claim 1, further comprising instructions for:

receiving a request from a second health practitioner to prescribe the first medication to a second patient;

detecting that the second patient is currently taking the second medication;

notifying the second health practitioner that there is a potential drug interaction between the first medication and second medication;

requiring the second health practitioner to confirm prescribing of the first medication before the first medication is prescribed.

7. The non-transitory computer-readable medium of claim 1, wherein the range of expected durations of the first medication course of treatment depends on patient demographic information.

8. The non-transitory computer-readable medium of claim 1, wherein the first medication and second medication treat the same condition.

9. The non-transitory computer-readable medium of claim 1, wherein the first medication and second medication treat different conditions.

10. The non-transitory computer-readable medium of claim 1, wherein the first medical event includes a billing code.

11. A non-transitory computer-readable medium comprising instructions for detecting interactions between medications, the non-transitory computer-readable medium comprising instructions for:

receiving, at a server over a network, first electronic records of a plurality of medical events of a patient, from a database, each of the medical events including a date and a text description, at least one of the medical events indicating the patient filling a prescription, at least one of the medical events indicating an appointment with a health provider, the first electronic records being of a first record type;

parsing, by a lexical analyzer implemented on the server, the received first electronic records into first tokens, wherein the lexical analyzer comprises a machine learning model and a natural language processing model, and wherein the tokenizing is based on results of the machine learning model and the natural language processing model, the first tokens having a first token type;

identifying a first medical event, from the tokenized first electronic records, wherein the first medical event comprises the patient filling a prescription for a first medication;

determining the presence of one or more medical events related to the first medical event in the tokenized first electronic records;

identifying, from the tokenized first electronic records, one or more related medical events associated with the first medication, wherein the one or more related medical events comprise the patient filling a prescription for the first medication;

determining that the first medical event indicates that the patient has started a course of treatment using the first medication based on the date associated with the first medical event, the presence determination and the related medical events, wherein the determining comprises:

determining a threshold period of time for the first medical event;

identifying one or more related events that fall within the determined threshold period of time;

receiving an expected refill interval for the prescription; and identifying the related medical events occurring after the first medical event, the related medical events occurring within the expected refill interval of at least one other of the related medical events or the first medical event;

determining, by the server, a duration of the first medication course of treatment of the patient based on statistically evaluating refill intervals of the related medical events, wherein the evaluating comprises:

calculating a maximum deviation value based on the time to fill for each related medical event;

detecting if each of the related medical events occurred within the calculated maximum deviation value of the expected refill interval;

calculating the time interval between the first medical event and the chronologically last of the related medical events, wherein the chronologically last of the related medical events is based on the detecting of related medical events within the calculated deviation value of the expected refill interval;

receiving, at the server, a notification from a pharmacy device, wherein the notification comprises a second electronic record that the patient is taking a second medication, the second electronic record being of a second record type different than the first record type;

parsing, by the lexical analyzer, the second electronic record into second tokens based on results of the machine learning model and the natural language processing model, the second tokens having a second token type that is the same as the first token type;

determining, based on the tokenized second electronic record, that the patient is taking the second medication during the first medication course of treatment;

identifying a range of expected durations of the first medication course of treatment;

determining if the duration of the first medication course of treatment is outside of the range of expected durations of the first medication course of treatment;

when it is determined that the duration of the first medication course of treatment is outside of the range of expected durations of the first medication course of treatment, storing, in the database, a value indicating a potential drug interaction;

retrieving, from the database, one or more potential drug interaction values;

determining, by interaction analysis, based at least partly on the retrieved potential drug interaction values, a percentage of times there was a detected potential drug interaction between the first medication and second medication compared to there being no detected drug interaction between the first medication and second medication to determine a percentage of time of detected drug interactions;

detecting, by interaction analysis, an interaction when the percentage of time of detected drug interactions exceeds an interaction detection threshold;

transmitting, from the server over the network, a notification to one or more health provider devices or one or more pharmacy devices, wherein the notification informs other health practitioners who prescribe the first medication that there is a potential interaction with the second medication; and adjusting, the interaction detection threshold in the interaction analysis, wherein the modifying is based on feedback indicating a correctly detected interaction.

12. The non-transitory computer-readable medium of claim 11, further comprising instructions for:
receiving ground-truth feedback for whether a detected drug interaction between the first medication and second medication is an actual drug interaction between the first medication and second medication;
adjusting the interaction detection threshold based on the ground-truth feedback.

13. The non-transitory computer-readable medium of claim 11, further comprising instructions for:
receiving user input of a desired level of statistical significance;
automatically adjusting the interaction detection threshold based on the desired level of statistical significance.

14. The non-transitory computer-readable medium of claim 11, further comprising instructions for:
detecting a drug interaction between the first medication and second medication for patients in a first demographic group but not for patients in a second demographic group.

15. The non-transitory computer-readable medium of claim 11, further comprising instructions for:
displaying the first electronic records of the plurality of medical events on a mobile device.

16. The non-transitory computer-readable medium of claim 11, further comprising instructions for:
receiving a request from a second health practitioner to prescribe the first medication to a second patient;
detecting that the second patient is currently taking the second medication;
notifying the second health practitioner that there is a potential drug interaction between the first medication and second medication;
requiring the second health practitioner to confirm prescribing of the first medication before the first medication is prescribed.

17. The non-transitory computer-readable medium of claim 11, wherein the range of expected durations of the first medication course of treatment depends on patient demographic information.

18. The non-transitory computer-readable medium of claim 11, wherein the first medication and second medication treat the same condition.

19. The non-transitory computer-readable medium of claim 11, wherein the first medication and second medication treat different conditions.

20. The non-transitory computer-readable medium of claim 11, wherein the first medical event includes a billing code.

* * * * *